United States Patent
Lazzaro

(10) Patent No.: US 11,351,024 B2
(45) Date of Patent: Jun. 7, 2022

(54) AIRWAY SUPPORT DEVICE

(71) Applicant: Lazzaro Medical, LLC, Boulder, CO (US)

(72) Inventor: Richard Lazzaro, Colts Neck, NJ (US)

(73) Assignee: Lazzaro Medical, LLC, Boulder, CO (US)

( * ) Notice: Subject to any disclaimer, the term of this patent is extended or adjusted under 35 U.S.C. 154(b) by 193 days.

(21) Appl. No.: 16/905,723

(22) Filed: Jun. 18, 2020

(65) Prior Publication Data

US 2020/0397560 A1 Dec. 24, 2020

Related U.S. Application Data

(60) Provisional application No. 62/864,929, filed on Jun. 21, 2019.

(51) Int. Cl.
*A61F 2/04* (2013.01)
*A61B 17/06* (2006.01)
*A61B 17/00* (2006.01)

(52) U.S. Cl.
CPC .......... *A61F 2/04* (2013.01); *A61B 17/06166* (2013.01); *A61B 2017/00004* (2013.01);
(Continued)

(58) Field of Classification Search
CPC .................. A61F 2/04; A61F 2002/042; A61F 2002/046; A61F 2/82; A61B 17/06166; A61B 2017/00004
USPC ...................................................... 623/15.11
See application file for complete search history.

(56) References Cited

U.S. PATENT DOCUMENTS 9,022,024 B2  5/2015 Dineen et al.
9,539,083 B2  1/2017 Eller et al.
(Continued)

FOREIGN PATENT DOCUMENTS

CN      202960836 U    6/2013
WO  WO 2008/006090    1/2008

OTHER PUBLICATIONS

International Search Report and Written Opinion from PCT/US2020/038534, dated Sep. 14, 2020, 14 pages.
(Continued)

*Primary Examiner* — Suzette J Gherbi
(74) *Attorney, Agent, or Firm* — Morgan, Lewis & Bockius LLP

(57) ABSTRACT

An airway support device of the present disclosure can be attached to tracheal and/or bronchial cartilage on opposing sides of a tracheal and/or bronchial wall to pull the tracheal and/or bronchial cartilages toward each other to reconstruct and/or reshape to a normal anatomy across the membranous tracheal and/or bronchial wall and thus relieving tension across the tracheal and/or bronchial wall. The airway support device can include at least two longitudinal strips that extend longitudinally along and are attached (e.g., sutured) to the trachea and/or bronchus on opposite sides of the tracheal and/or bronchial wall. Pairs of lateral strips extending from each of the longitudinal strips can be attached to each other under tension. The tracheal and/or bronchial wall can be attached (e.g., sutured) to the lateral strips to open the airway of the trachea and/or bronchus.

20 Claims, 11 Drawing Sheets

(52) U.S. Cl.
CPC ... *A61F 2002/043* (2013.01); *A61F 2002/046* (2013.01); *A61F 2220/0075* (2013.01); *A61F 2250/0097* (2013.01)

(56) References Cited

U.S. PATENT DOCUMENTS

| | | | | |
|---|---|---|---|---|
| 9,737,393 | B2* | 8/2017 | Fleury | A61F 2/04 |
| 10,449,026 | B2* | 10/2019 | Sostek | A61L 27/34 |
| 2010/0122698 | A1 | 5/2010 | Miller et al. | |
| 2012/0035715 | A1* | 2/2012 | Robida | A61F 2/848 |
| | | | | 623/1.36 |
| 2015/0230948 | A1* | 8/2015 | Riina | A61F 2/844 |
| | | | | 623/9 |
| 2016/0051385 | A1* | 2/2016 | Hollister | A61L 31/148 |
| | | | | 623/23.65 |
| 2016/0143724 | A1* | 5/2016 | Fleury | A61F 2/04 |
| | | | | 623/9 |
| 2017/0135796 | A1* | 5/2017 | Sostek | A61F 2/07 |
| 2019/0350731 | A1* | 11/2019 | Liu | A61F 2/91 |
| 2020/0054796 | A1* | 2/2020 | Kaplan | A61L 31/16 |
| 2020/0085557 | A1* | 3/2020 | Sostek | A61F 2/02 |
| 2020/0146803 | A1* | 5/2020 | Bertolino | A61F 2/07 |
| 2020/0163747 | A1* | 5/2020 | Park | A61L 27/222 |

OTHER PUBLICATIONS

Communication pursuant to Rules 161(1) and 162 EPC for Application No. 20739516.1, dated Jan. 28, 2022, 3 pages.

* cited by examiner

AIRWAY SUPPORT DEVICE

CROSS-REFERENCE TO RELATED APPLICATION

This application claims the benefit of U.S. Provisional Application No. 62/864,929, entitled "TRACHEAL SUPPORT DEVICE," filed Jun. 21, 2019, the entirety of which is incorporated herein by reference.

TECHNICAL FIELD

The present description relates generally to airway support devices, and, more particularly, to devices for adding structural support to improve an airway of a patient.

BACKGROUND

Tracheo-bronchial (or "airway") treatments can be performed to relieve difficult or labored breathing caused by a variety of conditions, including but not limited to extrinsic and/or intrinsic compression (e.g., stenosis), disease, and loss of cartilaginous support. Such treatments can relieve airway obstruction caused by strictures, injury, disease, or the like.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

A trachea and/or bronchus of the patient can experience stenosis and/or dynamic airway collapse in a manner that narrows an airway extending there through and restricts breathing of the patient. An airway support device of the present disclosure can be attached to tracheal and/or bronchial cartilage, or tissue adjacent to tracheal and/or bronchial cartilage, on opposing sides of a tracheal and/or bronchial wall to pull the tracheal and/or bronchial cartilage ends toward each other and relieve tension across the tracheal and/or bronchial wall and/or to reconstruct and/or reshape to normal anatomy across the membranous tracheal and/or bronchial wall.

An airway support device can include at least two longitudinal strips that extend longitudinally along and are attached (e.g., sutured) to the trachea and/or bronchus on opposing sides of the tracheal and/or bronchial wall. A pair or pairs of lateral strips extending from each of the longitudinal strips can be attached to each other under tension. The tracheal and/or bronchial wall can be attached (e.g., sutured) to the lateral strips to open and keep open the airway of the trachea and/or bronchus.

These and other embodiments are discussed below with reference to FIGS. 1-12. However, those skilled in the art will readily appreciate that the detailed description given herein with respect to these Figures is for explanatory purposes only and should not be construed as limiting.

Though many of the examples provided herein refer to devices for use within the airway, the present disclosure is also applicable to a variety of devices designed for a variety of applications in various lumens and/or openings of the body.

Figure 1:
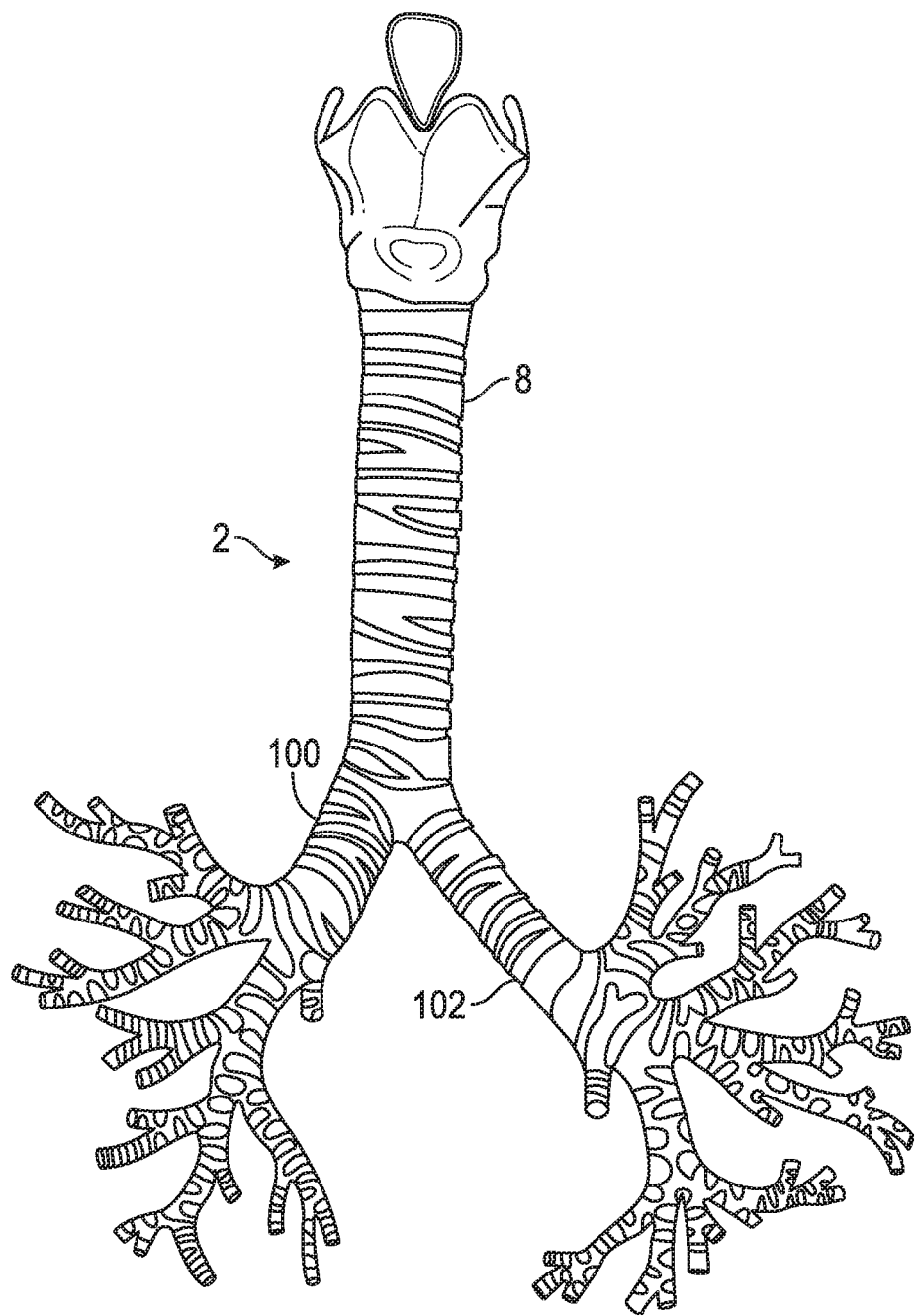
FIG. 1 shows an anterior view of a trachea with laryngeal structures and the bronchial tree, according to some embodiments of the present disclosure.

FIG. 1 depicts a trachea relative to the laryngeal structures and the bronchial tree. The trachea 2 courses from a subcutaneous position in the neck to a position against the esophagus and prevertebral fascia at the level of the carina. The carina bifurcates into the left and right mainstem bronchi 100 and 102 at the level of the fifth thoracic vertebral body and can be localized approximately at the same level as the sternal notch. There are typically about 18 to about 22 horseshoe-shaped cartilaginous rings (e.g., tracheal cartilages) 8 in the human trachea. The horseshoe-shaped rings give the tracheal wall (not shown in FIG. 1) of the trachea 2 a slightly flattened appearance. This tracheal wall is also known as the membranous trachea. The airway in an adult is roughly elliptical. The trachea 2 is not rigidly fixed to the surrounding tissue and provides relatively free vertical movement in relation to other anatomic structures.

Figure 2A:
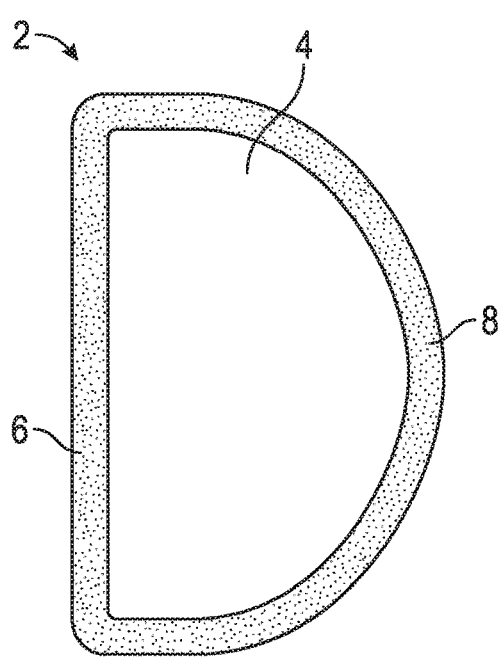
FIG. 2A illustrates a top sectional view of a trachea, in accordance with some embodiments of the present disclosure.
Figure 2B:
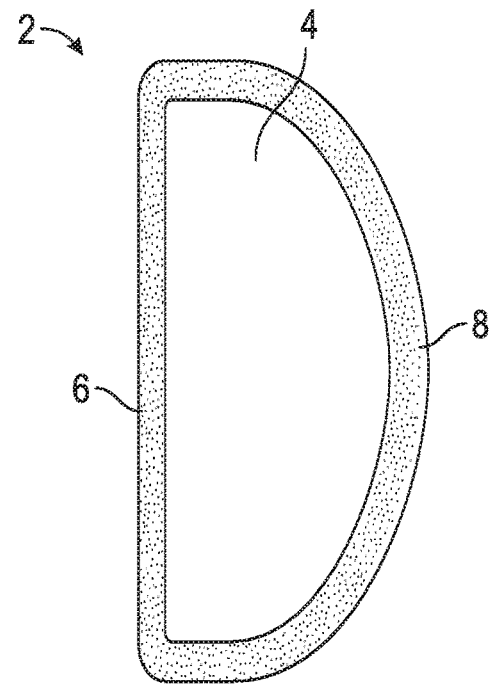
FIG. 2B illustrates a top sectional view of a trachea under the influence of tracheomalacia, in accordance with some embodiments of the present disclosure.
Figure 3:
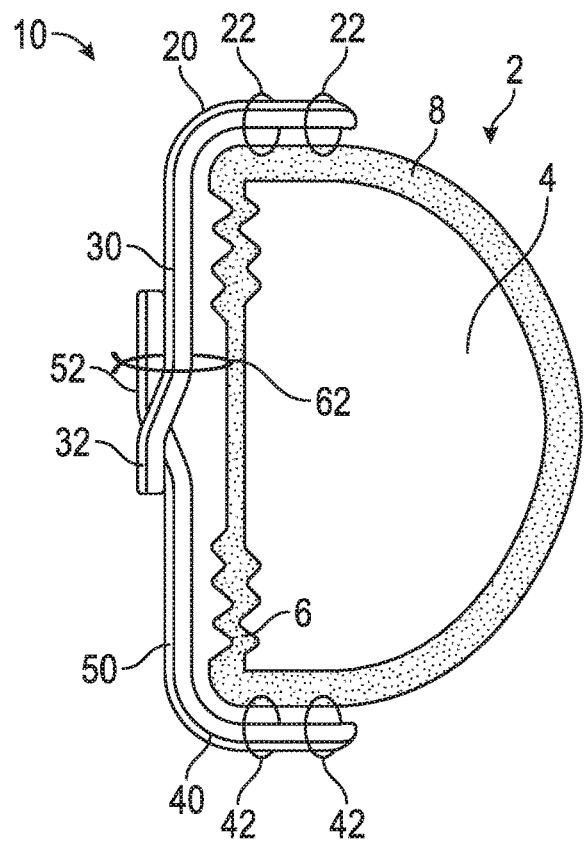
FIG. 3 illustrates a top sectional view of a trachea with an airway support device extending across the tracheal wall, in accordance with some embodiments of the present disclosure.

Referring now to FIGS. 2A, 2B, and 3, a trachea and/or bronchus of the patient can experience stenosis in a manner that narrows an airway extending there through and restricts breathing of the patient. While reference is made to a trachea and related tracheal structures as shown in FIGS. 2A, 2B, and 3, it will be understood that such description can additionally or alternatively be applied to a bronchus and related bronchial structures.

As shown in FIG. 2A, the trachea 2 includes an airway 4 between one or more regions of tracheal cartilage 8 and the tracheal wall 6. The tracheal cartilage 8 can generally form a horseshoe-shape or C-shape in cross section.

As shown in FIG. 2B, a trachea can undergo tracheomalacia, in which the flaccidity of the tracheal cartilage 8 leads to widening of the tracheal wall 6. As the tracheal wall 6 stretches, the airway 4 can narrow in at least one dimension (e.g., at least partially collapse), thereby restricting airflow through the airway 4. It will be understood that bronchomalacia can occur at the bronchi with similar effects.

As shown in FIG. 3, an airway support device can be provided to restore the size and/or shape of the airway of the trachea and/or the bronchi. For example, the conditions of the trachea and/or bronchi can be ameliorated following tracheomalacia and/or bronchomalacia.

An airway support device 10 can include a first longitudinal strip 20 on a first side of the trachea 2 and a second longitudinal strip 40 on a second side of the trachea 2, opposite the first side. The first longitudinal strip 20 can be sutured or otherwise attached to the tracheal cartilage 8 and/or adjacent or adjoining tissue, on the first side of the trachea 2 with sutures 22, and the second longitudinal strip 40 can be sutured or otherwise attached to the tracheal cartilage 8 and/or adjacent or adjoining tissue on the second side of the trachea 2 with sutures 42. The longitudinal strips can include holes extending there through for receiving a portion of the sutures. Additionally or alternatively, the longitudinal strips can include measurement reference markers or other visual feature for indicating a location where a suture is to be provided.

Multiple first lateral strips 30 can extend from the first longitudinal strip 20, and multiple second lateral strips 50 can extend from the second longitudinal strip 40. Each of the first lateral strips 30 can include a first attachment member 32, and each of the second lateral strips 50 can include a second attachment member 52. The first attachment member 32 and the second attachment member 52 are configured to engage each other to connect the first lateral strip 30 to the second lateral strip 50. This connection can further connect the first longitudinal strip 20 to the second longitudinal strip 40. The first longitudinal strip 20 and the second longitudinal strip 40 can be pulled towards each other to allow the first attachment member 32 and the second attachment member 52 to engage each other. The first attachment member 32 and the second attachment member 52 can remain engaged while the first lateral strips 30 and the second lateral strip 50 are under tension. In this configuration, the opposing sides of the trachea 2 can be pulled towards each other, and the tracheal wall 6 can be reduced in width. The airway 4 can thereby be enlarged (e.g., in cross-sectional dimension).

The tracheal wall 6 can be further supported in a manner that prevents it from collapsing into the airway 4. For example, the first lateral strips 30 (optionally including the first attachment member 32) and/or the second lateral strip 50 (optionally including the second attachment member 52) can be sutured or otherwise attached to the tracheal wall 6 with one or more sutures 62. The lateral strips can include holes extending there through for receiving a portion of the sutures. Additionally or alternatively, the lateral strips can include a marker or other visual feature for indicating a location where a suture is to be provided. While the tracheal wall 6 may be loose (e.g., slackened) due to the reduction in its width, the one or more sutures 62 can retain the tracheal wall 6 against the corresponding lateral strip(s) so that it does not collapse into the airway 4.

Figure 4:
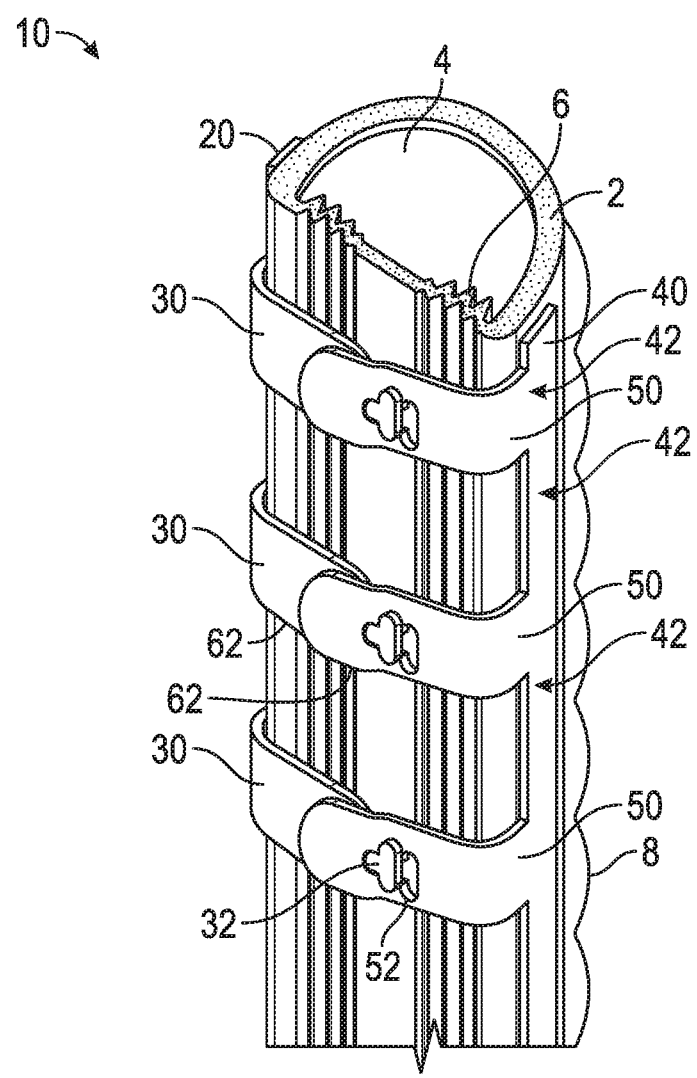
FIG. 4 illustrates a perspective view of a trachea with an airway support device extending across the tracheal wall, in accordance with some embodiments of the present disclosure.

Referring now to FIG. 4, multiple lateral strips can be connected together to provide support at various locations along a length of the trachea and/or bronchus. While reference is made to a trachea and related tracheal structures as shown in FIG. 4, it will be understood that such description can additionally or alternatively be applied to a bronchus and related bronchial structures.

As shown in FIG. 4, the first longitudinal strip 20 can be attached to a first side of the trachea 2 and the second longitudinal strip 40 can be attached to a second side of the trachea 2, opposite the first side. Each longitudinal strip can be sutured or otherwise connected with multiple sutures, such that the longitudinal strips are connected to the trachea 2 at multiple longitudinal locations.

As further shown in FIG. 4, each of the first longitudinal strip 20 and the second longitudinal strip 40 can include multiple lateral strips that are connected together. By further example, the first longitudinal strip 20 can extend along a longitudinal length of the trachea 2 (e.g., across multiple tracheal cartilages 8) and provide multiple first lateral strips 30 extending laterally across the tracheal wall 6. The second longitudinal strip 40 can extend along the longitudinal length of the trachea 2 (e.g., across multiple tracheal cartilages 8) and provide multiple second lateral strips 50 extending laterally across the tracheal wall 6. Accordingly, each corresponding pair of a first lateral strip 30 and a second lateral strip 50 can be placed under tension and pull on a corresponding section of the trachea 2 at a particular longitudinal location thereof.

It will be understood that any number of lateral strips and or pairs of lateral strips can be provided. Each longitudinal strip can include 1, 2, 3, 4, 5, 6, 7, 8, 9, 10, or more than 10 lateral strips. The lateral strips can be evenly or unevenly distributed along a longitudinal length of the corresponding longitudinal strip. Each lateral strip can attach to only one other lateral strip. Alternatively, each lateral strip can attach to more than one other lateral strip.

Figure 5:
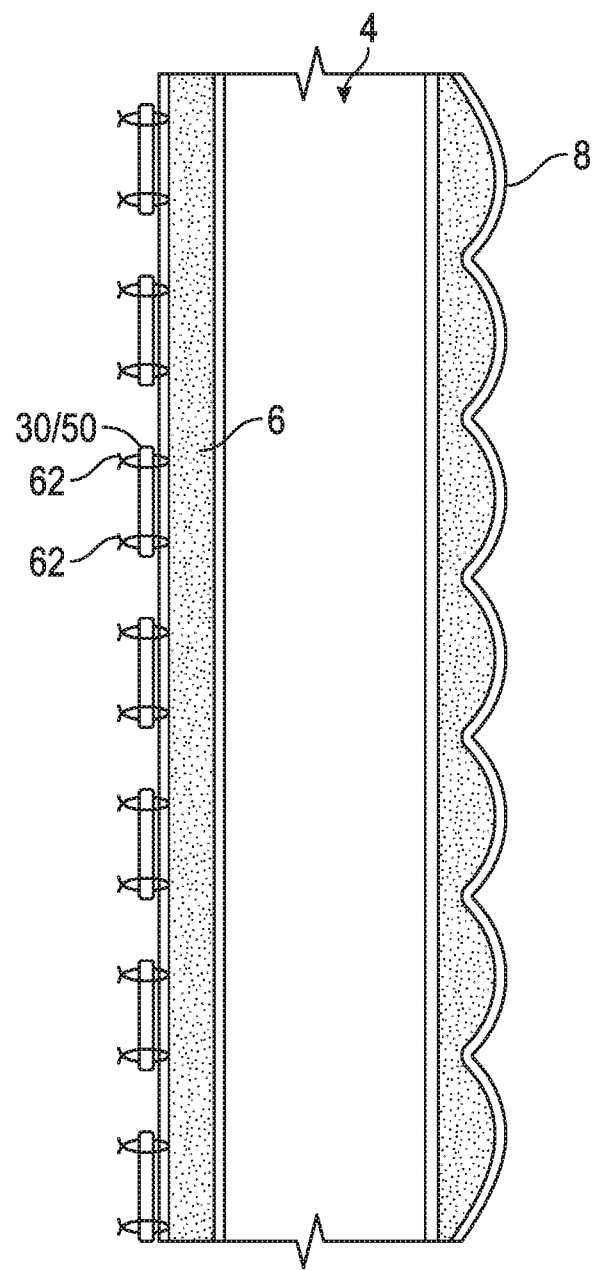
FIG. 5 illustrates a side sectional view a trachea with an airway support device extending across the tracheal wall, in accordance with some embodiments of the present disclosure.

Referring now to FIG. 5, multiple lateral strips can be connected to the tracheal and/or bronchial wall. While reference is made to a trachea and related tracheal structures as shown in FIG. 5, it will be understood that such description can additionally or alternatively be applied to a bronchus and related bronchial structures.

As shown in FIG. 5, the first lateral strip 30 and/or the second lateral strip 50 can be sutured or otherwise attached to the tracheal wall 6 with sutures 62. Accordingly, the lateral strips can be directly connected (e.g., sutured) to the tracheal wall 6 at multiple longitudinal locations. The sutures 62 can hold the lateral strips against the tracheal wall 6. Likewise, the tracheal wall 6 can be held in a taught configuration in it is juxtaposed against the lateral strips. As such, the airway 4 can be enlarged by avoiding collapse of the tracheal wall 6 away from the lateral strips and into the airway 4.

Figure 6:
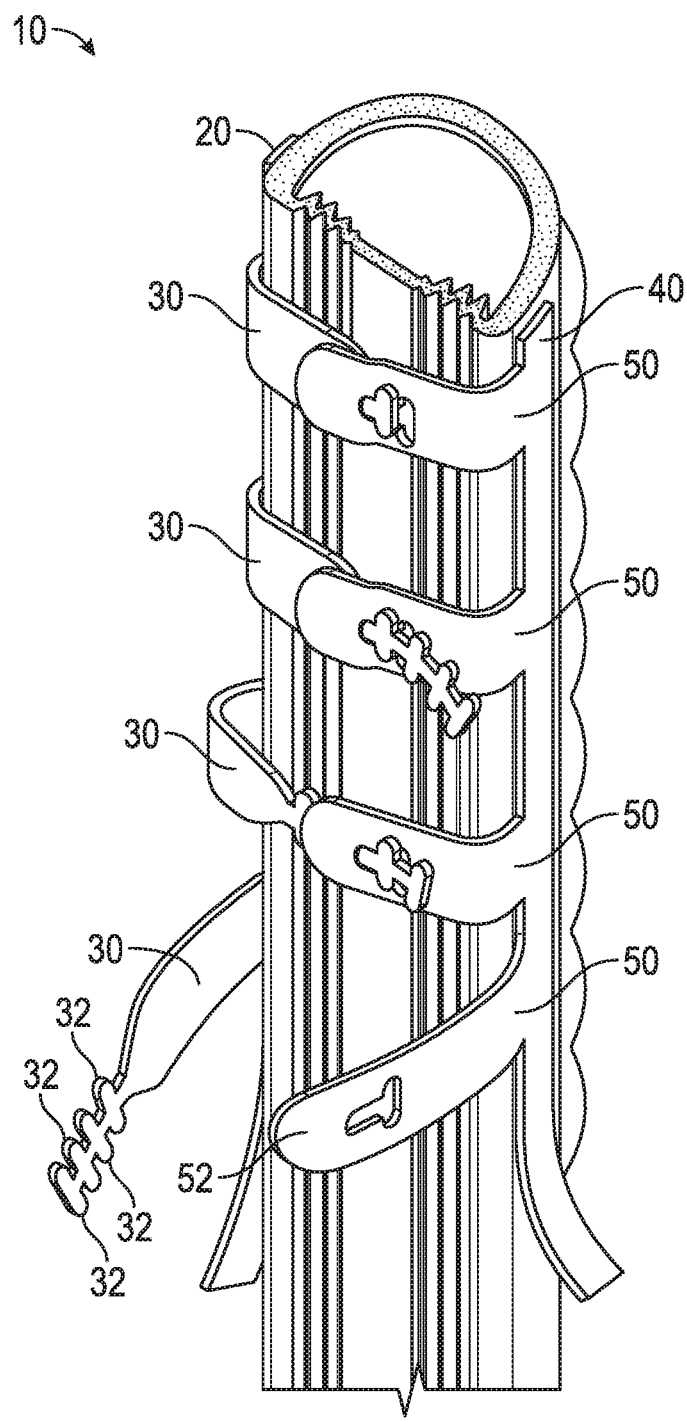
FIG. 6 illustrates a perspective view of a trachea with an airway support device extending across the tracheal wall, according to some embodiments of the present disclosure.

Referring now to FIG. 6, the attachment members of the lateral strips can engage each other with customizable and adjustable capabilities. For example, as shown in FIG. 6, the first attachment members 32 and/or the second attachment members 52 can facilitate engagement at various relative positions. For example, the first attachment member 32 can engage the second attachment member 52 at one of a variety of positions and/or portions thereof. The different engagement options can correspond to different alignments (e.g., amounts of overlap) between the first attachment member 32 and the second attachment member 52. Accordingly, the tightness (e.g., amount of tension) of the attachment members can be determined by the positions selected.

As further shown in FIG. 6, each pair of lateral strips can be provided with a tightness that is independent of one or more other pairs of lateral strips. For example, a first pair of lateral strips can be engaged with corresponding attachment members in a first configuration, and a second pair of lateral strips can be engaged with corresponding attachment members in a second configuration. Accordingly, the airway support device 10 can provide different forces at different longitudinal positions along the trachea and/or bronchus.

One or more components (e.g., strips) of an airway support device can be formed as a mesh, a woven structure, a knitted structure, a sheet, a patch, a monolith body, a set of interconnected parts, and/or a combination thereof. The components can be formed by one or more of a variety of materials. Such materials can include one or more polymers, one or more metals or metal alloys (e.g., stainless steel, titanium, a shape-memory alloy, a nickel-titanium allow, Nitinol, magnetic materials, ferromagnetic materials, etc.), one or more ceramics, and/or a combination thereof. Polymer materials can include but are not limited to polyacrylic acid and polyacrylates such as polymethylmethacrylate, polybutylmethacrylate, polyacrylamide, polyacrylonitriles, polyamides, high-density polyethylene fibers (e.g., Tyvek®), polyetheramides, polyethylene amine, polyimides, polycarbonates, polycarbourethanes, polyvinyl ketones, polyvinyl halides, polyvinylidene halides, polyvinyl ethers, polyvinylarenes, polyvinyl esters, polyvinyl pyrrollidones, polyoxymethylenes, polyethylene, polypropylene, polytetrafluoro-ethylene (PTFE) (e.g., Teflon, Gore-Tex®), polyurethanes, polyolefine elastomers, polyisobutylenes, EPDM gums, fluorosilicones, carboxymethyl chitosans, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulphones, polyethersulphones, epoxy resins, ABS resins, silicones such as polysiloxanes, polyvinyl halogens and copolymers, cellulose ethers, cellulose triacetates, chitosan, chitosan derivatives, polymerizable oils such as linseed oil, polyvalerolactones, poly-ε-decalactones, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerates, poly(1, 4-dioxane-2,3-diones), poly(1,3-dioxane-2-one), poly-para-dioxanones, polyanhydrides such as polymaleic acid anhydrides, polyhydroxymethacrylates, fibrin, polycyanoacrylates, polycaprolactone-dimethylacrylates, poly-β-maleic acid, polycaprolactonebutyl-acrylates, multiblock polymers such as from oligocaprolactonedioles and oligodioxanonedioles, polyetherester multiblock polymers such as PEG and poly(butyleneterephthalate), polypivotolactones, polyglycolic acid (e.g., polyglactin 910, Vicryl®), polyglycolic acid trimethyl-carbonates, polycaprolactone-glycolides, poly(γ-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethylcarbonates, polyiminocarbonates, poly(N-vinyl)-pyrrolidone, polyvinylalcohols, polyesteramides, glycolated polyesters, polyphosphoesters, polyphosphazenes, poly[p-carboxyphenoxy) propane], polyhydroxypentanoic acid, polyanhydrides, polyethylene oxide-propylene oxide, soft polyurethanes, polyurethanes with amino acid residues in the backbone, polyetheresters such as polyethylene oxide, polyalkeneoxalates, polyorthoesters as well as copolymers thereof, carageenanes, fibrinogen, starch, collagen, protein based polymers, polyamino acids, synthetic polyamino acids, zein, modified zein, polyhydroxyalkanoates, pectic acid, actinic acid, modified and unmodified fibrin and casein, carboxymethyl sulphate, albumin, furthermore hyaluronic acid, heparan sulphate, heparin, chondroitine sulphate, dextran, β-cyclodextrins, and copolymers with PEG and polypropylene glycol, gummi arabicum, guar, gelatine, collagen, collagen-N-Hydroxysuccinimide, modifications and copolymers and/or mixtures of the substances mentioned above.

The sutures described herein can be of a material that is the same as a material for the strips and/or a different material. The sutures can be a non-absorbable material. The strips and/or the sutures can be absorbable, bioabsorable, and/or biodegradable.

Figure 7:
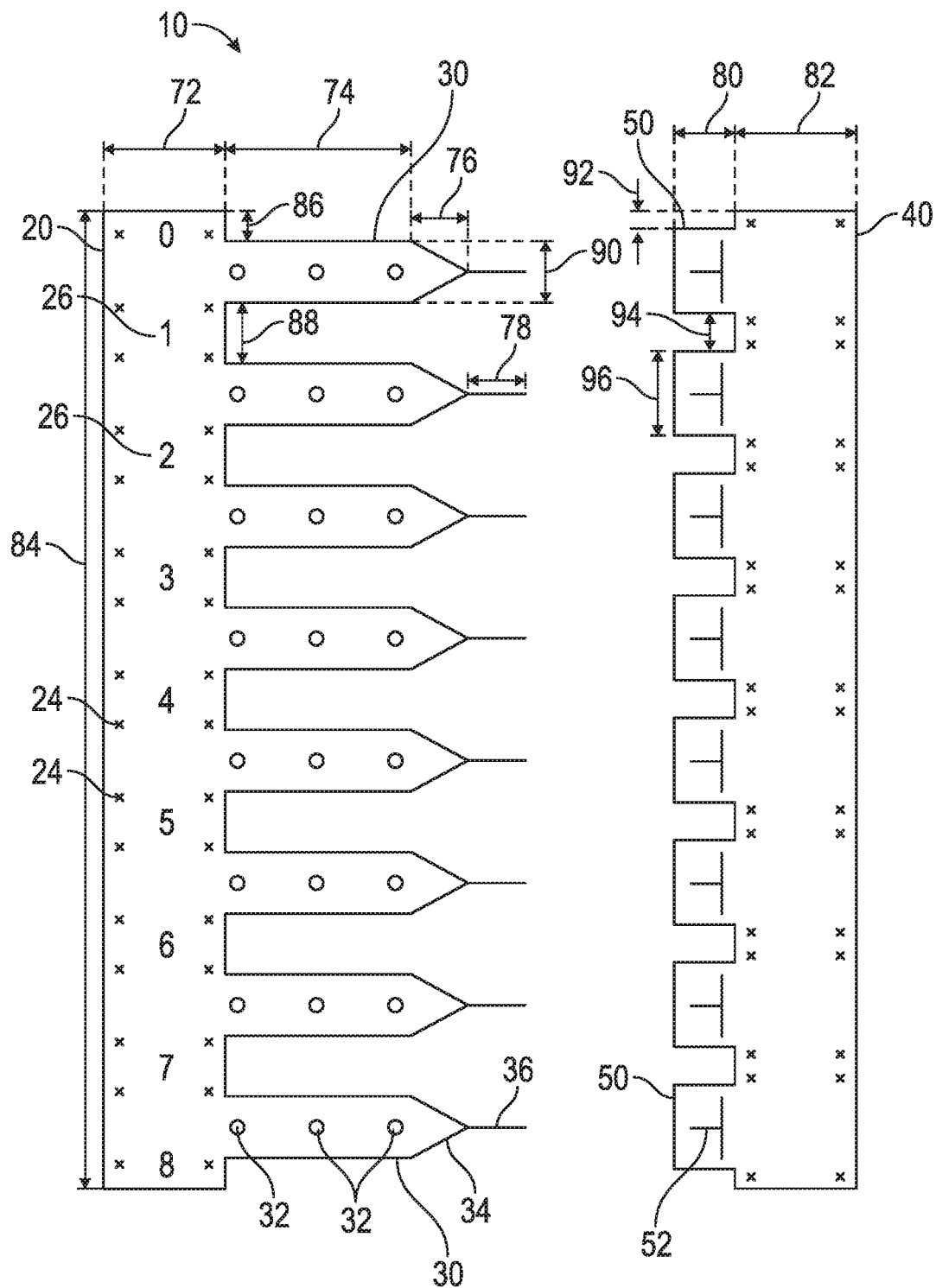
FIG. 7 illustrates a front view of an airway support device, according to some embodiments of the present disclosure.

Referring now to FIG. 7, the attachment members of the lateral strips can engage each other with one or more of a variety of mechanisms for providing customizable and adjustable capabilities. FIG. 7 illustrates a front view of an airway support device, according to some embodiments of the present disclosure. It will be understood that the airway support device of FIG. 7 can be related to the airway support device of FIGS. 3-6, having at least some features in common. Accordingly, the airway support device of FIG. 7 can be used in the manner illustrated in FIGS. 3-6.

As shown in FIG. 7, the longitudinal strips 20, 40 can each have a length 84 (e.g., 3-12 cm) and a width 72 (e.g., 0.5-2 cm). As used herein, the length 84 is measured along the longitudinal strips 20, 40 in a direction that is across multiple lateral strips 30, 50. As used herein, the width 72 is measured across the longitudinal strips 20, 40 in a direction that is toward the lateral strips 30, 50. The length 84 and/or width 72 can be constant or variable.

Each of the lateral strips 30, 50 can be separated from a neighboring one of the lateral strips 30, 50 by a gap 88 or 94. The gaps 88, 94 can be the same or different than each other (e.g., with the lateral strips 30, 50 evenly or unevenly distributed). Optionally, the longitudinal strips 20, 40 can provide a length 86 or 92 (e.g., 0.25-4 cm) that extends beyond an end one of the lateral strips 30, 50. Such lengths 86 and 92 can provide regions for suturing the longitudinal strips 20, 40.

The lateral strips 30, 50 can each have a length 74 or 80 (e.g., 0.25-3 cm) and a width 90 or 96 (e.g., 0.25-1 cm). As used herein, the length 74 is measured along each of the lateral strips 30, 50 in a direction that is away from a corresponding longitudinal strip 20 or 40 and/or toward an opposite lateral strip. As used herein, the width 90 or 96 is measured parallel to the longitudinal strips 20, 40. The lengths 74 or 80 can be the same or different from each other. The lengths 74 or 80 can be constant or variable. The widths 90 or 96 can be the same or different from each other. The widths 90 or 96 can be constant or variable.

Where the lateral strips 30 feed into openings 52 of the lateral strips 50, the lateral strips 30 can provide mechanisms to facilitate entry into the openings 52. For example, the lateral strips 30 can have at terminal ends thereof a thread 36 of a length 78 (e.g., 0.5-2 cm). Such a thread can be more easily inserted into an opening 52 than a larger portion of the corresponding lateral strip 30. Additionally or alternatively, the lateral strips 30 can include a transition portion 34 having a length 76 (e.g., 0.5-2 cm) along which the width transitions from a larger width (e.g., width 90) to a smaller width (e.g., to a point or zero). The transition portion 34 can form a taper, curve, or rounded end. Where no thread 36 is provided, the transition portion 34 can form a terminal end of the lateral strip 30.

While the dimensions described herein provide some examples, it will be understood that one or more of the dimensions described herein can be modified to suit any desired purpose. Dimensions can extend outside of the example ranges provided (e.g., above and/or below the example ranges). For example, any one or more of the structures described herein can be modified to match the desired target areas for assembly and placement. Accordingly, such dimensions can be modified according to variations in patient anatomy and/or conditions presented.

As further shown in FIG. 7, each of the first lateral strips 30 can include one or more first attachment members 32, and each of the second lateral strips 50 can include a second attachment member 52. The first attachment members 32 can include protrusions (e.g., posts, balls, pom poms, bumps, knots, extensions, and the like) that extend from a surface of a main body of the lateral strip 30. The second attachment members 52 can include an opening. The protrusions can extend into and/or through a corresponding one of the openings to hold the lateral strips 30, 50 in a fixed relative position. While multiple protrusions can be provided on each first lateral strip 30, only one opening may be provided on each second lateral strip 50. Each opening of the second lateral strips 50 can be smaller on a side that faces the first lateral strips 30, so that, under tension, the selected one of the protrusions is retained within and/or through the corresponding opening. The openings can be T-shaped, tapered, triangular, and the like to facilitate capture and retention of the protrusions.

The longitudinal strips 20, 40 and/or the lateral strips 30, 50 can provide measurement reference markers or other indicators to guide placement thereof. For example, the longitudinal strips 20, 40 and/or the lateral strips 30, 50 can include a number of reference markers 26 to indicate measurements (e.g., length).

On the longitudinal strips 20, 40, such reference markers 26 can indicate a length of the corresponding longitudinal strip 20 or 40 that relates to the number of lateral strips 30 or 50 extending from the corresponding longitudinal strip 20 or 40. The reference markers 26 can be used to reference a length of material desired, where an excess length can be removed (e.g., cut) from the longitudinal strips 20, 40.

On the lateral strips 30, 50, reference markers can indicate a length across a corresponding portion of the lateral strip, so that attachment at a given reference marker indicates to a user that the corresponding length of the lateral strip is in use. Accordingly, the user can select the desired length and align the attachment elements with the appropriate reference markers. It will be understood that the attachment elements themselves can serve as such reference markers.

The reference markers 26 and/or the material of the longitudinal strips 20, 40 and/or the lateral strips 30, 50 can vary to provide indications of length, dimensions, or another feature for reference by a user. For example, the reference markers 26 can include alpha-numerical characters. By example, the reference markers 26 can include one or more symbols. By example, the reference markers 26 can include one or more colors and/or color variations to visually distinguish one region of the longitudinal strips 20, 40 and/or the lateral strips 30, 50 from another region thereof. Such color and/or color variation can be achieved by the properties of the mesh material itself, such as with dyed fabric, a photo-reactive dye, and/or a fluorescent dye that can emit light when and/or after a light source (e.g., black, blue, fluorescent, and/or other) is presented.

Additionally or alternatively, the suture markers 24 can be provided to indicate the target location for suturing. The suture markers 24 can be provided at locations along the longitudinal strips 20, 40 to visually indicate where sutures can be preferably applied to secure the longitudinal strips 20, 40 to cartilage or other anatomy. For example, the suture markers 24 can include one or more symbols. By example, the suture markers 24 can include one or more colors and/or color variations to visually distinguish one region of the longitudinal strips 20, 40 and/or the lateral strips 30, 50 from another region thereof. Such color and/or color variation can be achieved by the properties of the mesh material itself, such as with dyed fabric, a photo-reactive dye, and/or a fluorescent dye that can emit light when and/or after a light source (e.g., black, blue, fluorescent, and/or other) is presented.

Color features described herein can refer to the mesh of the device, markers thereon, and/or sutures applied thereto. Two or more colors can be different so as to be distinguishable from each other (e.g., contrasting). For example, the mesh of a base portion (e.g., majority) of the device can be of a first color, and one or more reference markers 26 and/or one or more suture markers 24 can be of a second color, different and distinguishable from the first color. Two or more colors can be the same or similar so as to appear visually similar to each other (e.g., matching). For example, sutures or other components can be of a color that matches the suture markers 24. As such, the user can match sutures to corresponding suture markers of the same color. Where multiple colors are used, each color can correspond to a different pair or set of sutures and suture markers. This may help the user identify where each suture should be placed as well as track usage of remaining, unused sutures. The sutures can be provided in a kit that can optionally include the device having suture markers.

The colors and/or materials can be selected to emit light in response to light applied to the material. For example, the material can be a fluorescent material that emits light of one type when exposed to light of a different type. An applied light can be absorbed by the material, and a light of a different (e.g., longer) wavelength can be emitted. By further example, the material can be a phosphorescent material that emits light for a duration of time after the applied light is removed. By further example, the colors can be selected to contrast neighboring anatomy to present as readily recognizable and distinguishable. Optionally, the color and/or other feature of a given suture marker 24 can correspond to a color and/or other feature of a suture to be applied at the location of the given suture marker 24. Accordingly, the user can be guided to a particular location for applying each one of the sutures.

Figure 8:
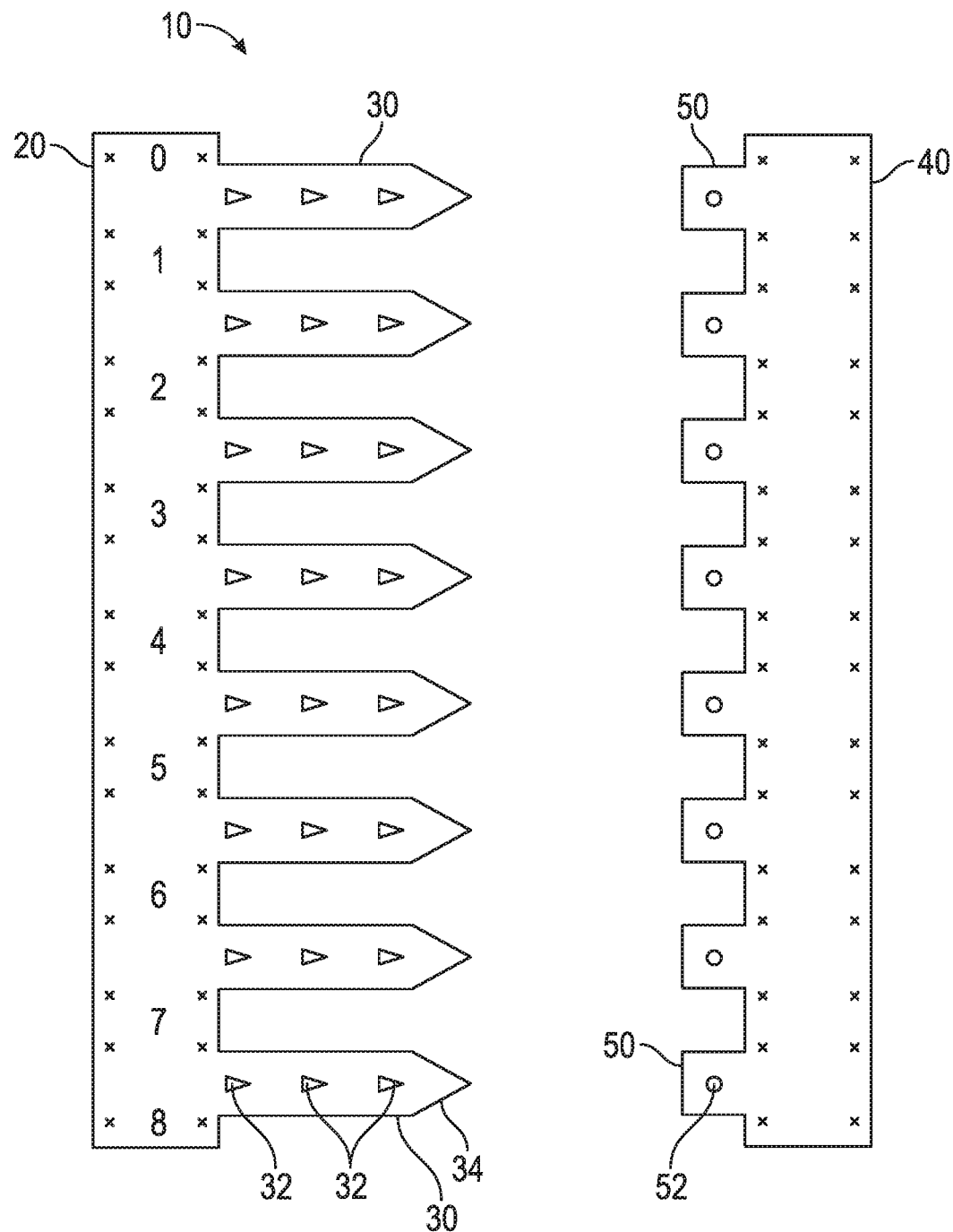
FIG. 8 illustrates a front view of an airway support device, according to some embodiments of the present disclosure.

Referring now to FIG. 8, the attachment members of the lateral strips can engage each other to provide customizable and adjustable capabilities. FIG. 8 illustrates a front view of an airway support device, according to some embodiments of the present disclosure. It will be understood that the airway support device of FIG. 8 can be related to the airway support device of FIGS. 3-6, having at least some features in common. Accordingly, the airway support device of FIG. 8 can be used in the manner illustrated in FIGS. 3-6.

As shown in FIG. 8, each of the first lateral strips 30 can include one or more first attachment members 32, and each of the second lateral strips 50 can include a second attachment member 52. The first attachment members 32 can include openings. The second attachment members 52 can include protrusions (e.g., posts, balls, pom poms, bumps, knots, extensions, and the like) that extend from a surface of a main body of the second lateral strip 50. The protrusions can extend into and/or through a corresponding one of the openings to hold the lateral strips 30, 50 in a fixed relative position. While multiple openings can be provided on each first lateral strip 30, only one protrusion may be provided on each second lateral strip 50. Each opening of the first lateral strips 30 can be smaller on a side that faces the second lateral strips 50, so that, under tension, the protrusion is retained within and/or through the selected one of the openings. The openings can be T-shaped, tapered, triangular, and the like to facilitate capture and retention of the protrusions.

As further shown in FIG. 8, it will be understood that the first lateral strips 30 are not inserted into an opening. Accordingly, threads can be omitted. Excess portions of the first lateral strips 30 can be secured or removed as described further herein.

Figure 9:
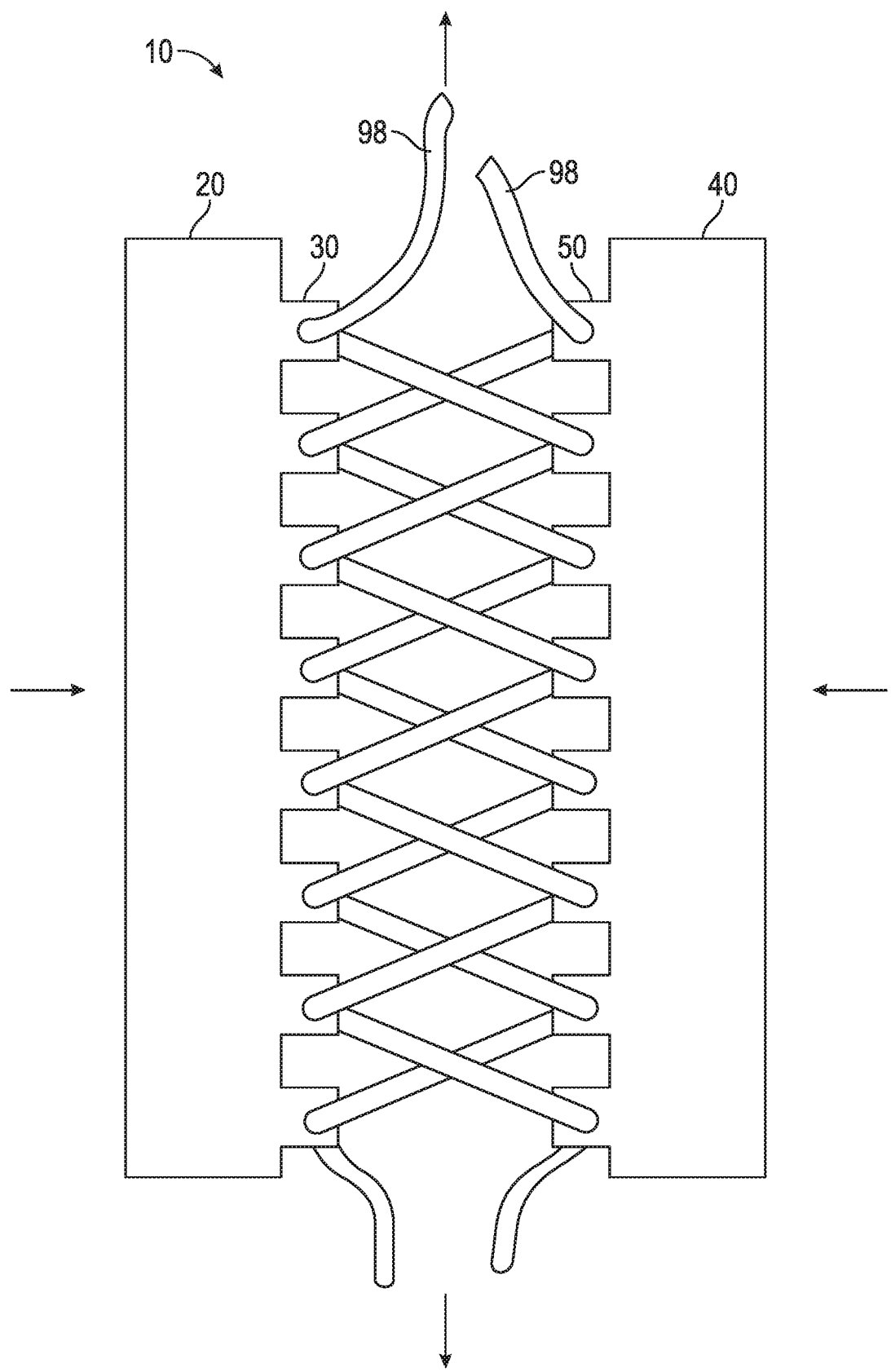
FIG. 9 illustrates a front view of an airway support device, according to some embodiments of the present disclosure.

Referring now to FIG. 9, the attachment members of the lateral strips can engage each other to provide customizable and adjustable capabilities. FIG. 9 illustrates a front view of an airway support device, according to some embodiments of the present disclosure. It will be understood that the airway support device of FIG. 9 can be related to the airway support device of FIGS. 3-6, having at least some features in common. Accordingly, the airway support device of FIG. 9 can be used in the manner illustrated in FIGS. 3-6.

As shown in FIG. 9, the first longitudinal strip 20 can have first lateral strips 30, and the second longitudinal strip 40 can have second lateral strips 50. The first lateral strips 30 and the second lateral strips 50 can be coupled together by one or more cords 98 that are threaded or laced through the lateral strips 30 and 50. The distance between the first longitudinal strip 20 and the second longitudinal strip 40 can be adjusted by pulling ends of the one or more cords 98, such that the total length of the cords 98 between the first longitudinal strip 20 and the second longitudinal strip 40 is decreased. As such, the tightness of the airway support device 10 can be adjusted as desired. It will be understood that only one or more than one cord 98 can be provided. In some embodiments, the cords 98 can serve as lateral strips, where the cords are laced directly through the longitudinal strips. While the individual pairs of lateral strips 30, 50 may be adjusted collectively, rather than individually, the tension across different pairs of lateral strips 30, 50 can be readily distributed as needed to conform to the anatomy.

While various attachment mechanisms are described herein, it will be understood that the attachment members can be any one or more of a variety of mechanisms. Such mechanisms can include, but are not limited to, locks, latches, buttons, holes, grooves, snaps, screws, clasps, threads, magnets, pins, adhesive, glue, and/or combinations thereof. The engagement of the attachment members can be reversible. The engagement of the attachment members can be maintained until controllably released.

Figure 10:
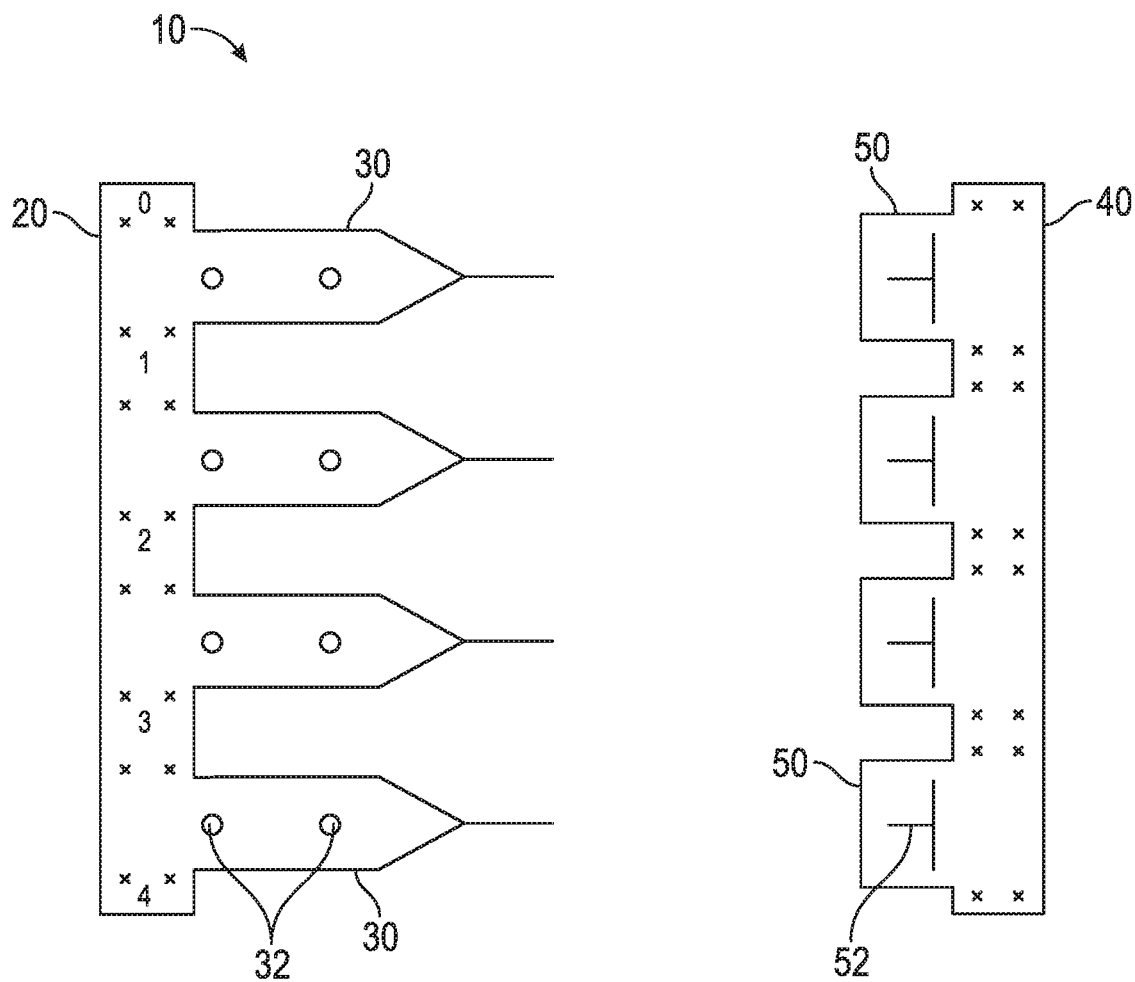
FIG. 10 illustrates a front view of an airway support device, according to some embodiments of the present disclosure.

Referring now to FIG. 10, an airway support device can be provided with one of various sizes and shapes. FIG. 10 illustrates a front view of an airway support device, according to some embodiments of the present disclosure. It will be understood that the airway support device of FIG. 10 can be related to the airway support device of FIGS. 3-6, having at least some features in common. Accordingly, the airway support device of FIG. 10 can be used in the manner illustrated in FIGS. 3-6.

The airway support device 10 of FIG. 10 can be smaller than at least one other airway support device. For example, an airway support device 10 can be provided for bronchial application, rather than tracheal application. As such, the airway support device 10 can have a size and shape that is appropriate for such bronchial application.

As shown in FIG. 10, the longitudinal strips 20, 40 can have a length that is shorter than longitudinal strips for tracheal applications. The lateral strips 30, 50 can also have lengths that are shorter than longitudinal strips for tracheal applications. Optionally, the first lateral strips 30 can have fewer first attachment members 32 to accommodate shorter lengths.

Figure 11:
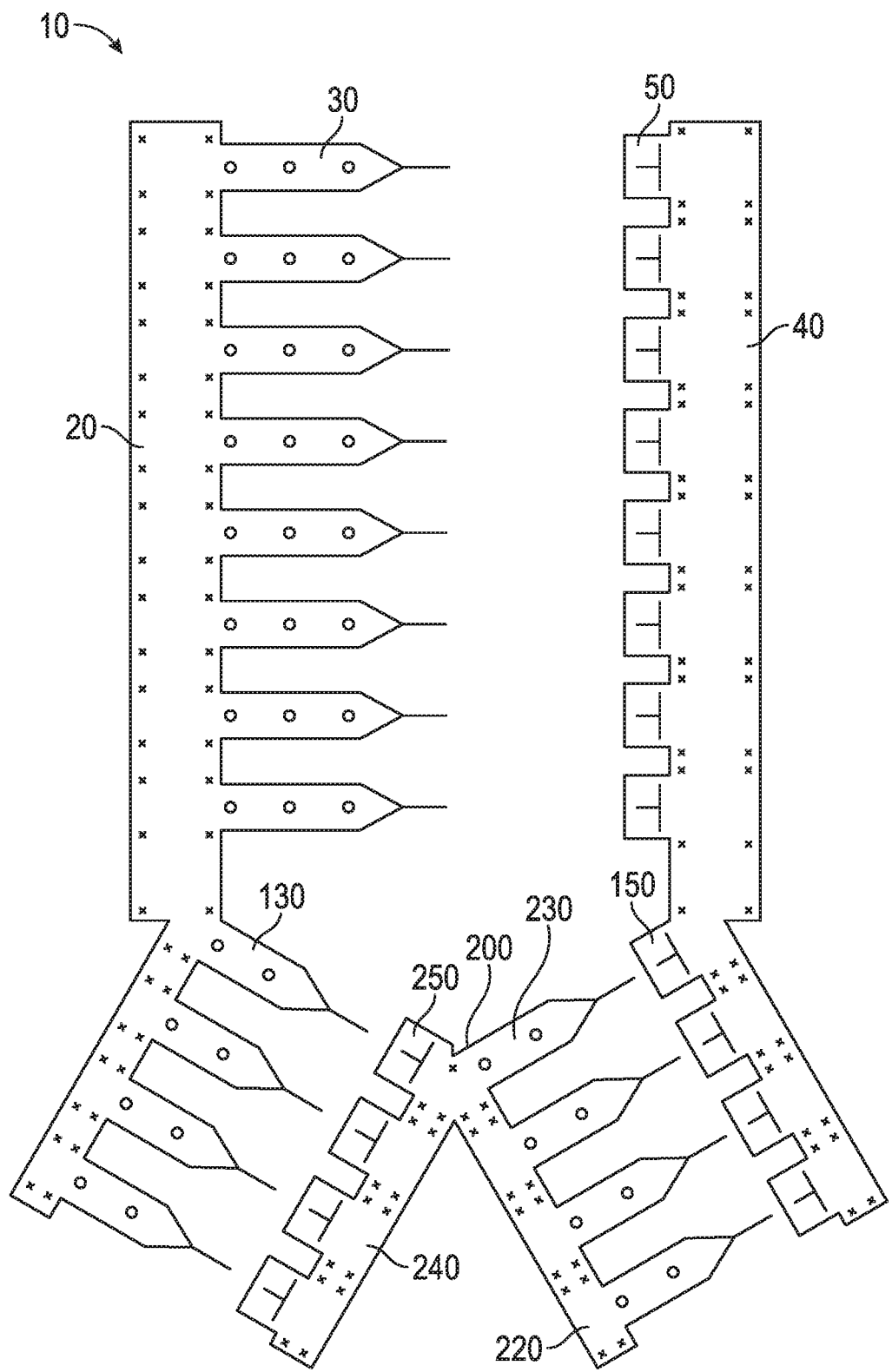
FIG. 11 illustrates a front view of an airway support device, according to some embodiments of the present disclosure.
Figure 12:
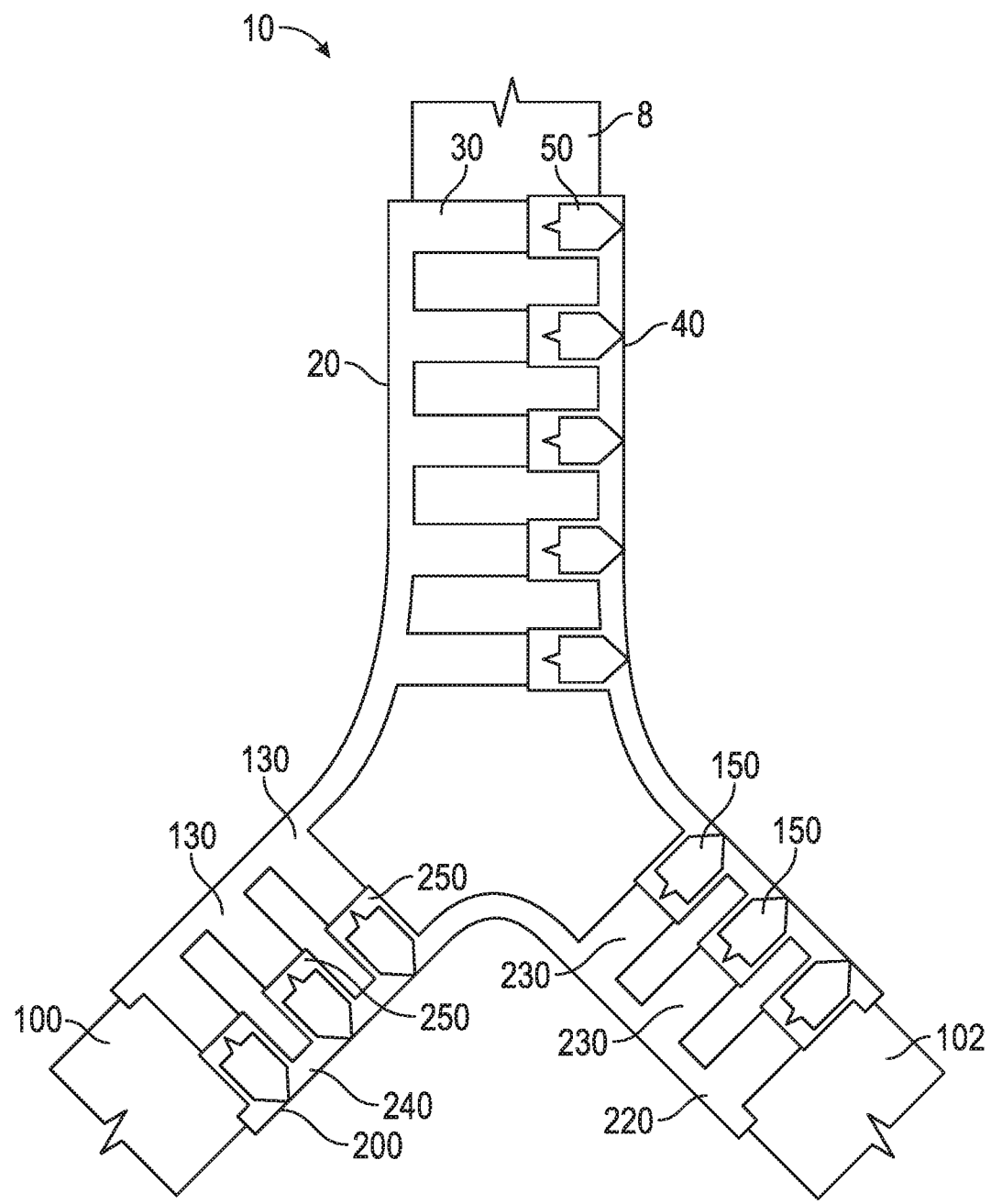
FIG. 12 illustrates a front view of a trachea and bronchi with the airway support device of FIG. 11 extending across the tracheal wall and bronchial walls, according to some embodiments of the present disclosure.

Referring now to FIGS. 11 and 12, an airway support device can be applied to both a trachea and one or more bronchi to provide support along an extended region of an airway. While the airway support device can be applied to an external surface of a trachea, it will be understood that a device having the features described herein can be applied to one or more other structures, including bronchi. For example, a support device can be applied to an external surface of a trachea and/or one or more bronchi. Multiple longitudinal and/or lateral strips can be provided to extend across the desired target structures.

FIG. 11 illustrates a front view of an airway support device, according to some embodiments of the present disclosure. FIG. 12 illustrates a front view of a trachea and bronchi with the airway support device of FIG. 11 extending across the tracheal wall and bronchial walls, according to some embodiments of the present disclosure.

As shown in FIGS. 11 and 12, an airway support device 10 can include a first longitudinal strip 20 on a first side of the trachea 2 and a second longitudinal strip 40 on a second side of the trachea 2, opposite the first side, as described herein. Multiple first lateral strips 30 (e.g., tracheal lateral strips) can extend from the first longitudinal strip 20, and multiple second lateral strips 50 (e.g., tracheal lateral strips) can extend from the second longitudinal strip 40.

As further shown in FIGS. 11 and 12, the first longitudinal strip 20 can further extend to an outer side of a first bronchi 102, and the second longitudinal strip 40 can further extend to an outer side of a second bronchi 100. From these regions, first bronchial lateral strips 130 and second bronchial lateral strips 150 can extend across the bronchi 100, 102.

A third longitudinal strip 220 can extend along an inner side of the second bronchi 100. One or more third bronchial lateral strips 230 can extend from the third longitudinal strip 220 and engage the second bronchial lateral strips 150 in corresponding pairs. The third bronchial lateral strips 230 and the second bronchial lateral strips 150 can engage each other in a manner described herein with respect to other attachment mechanisms for lateral strips.

A fourth longitudinal strip 240 can extend along an inner side of the first bronchi 102. One or more fourth bronchial lateral strips 250 can extend from the fourth longitudinal strip 240 and engage the first bronchial lateral strips 130 in corresponding pairs. The fourth bronchial lateral strips 250 and the first bronchial lateral strips 130 can engage each other in a manner described herein with respect to other attachment mechanisms for lateral strips.

The third longitudinal strip 220 and the fourth longitudinal strip 240 can be provided as a continuous strip (e.g. of mesh). Alternatively, third longitudinal strip 220 and the fourth longitudinal strip 240 can be distinct strips that are separated by a gap to facilitate relative movement there between.

A method can be performed to implant an airway support device as described herein. The method can include the steps described herein, which can be performed in any order. It will be understood that steps described herein can be omitted and/or substituted by yet other steps. It will be understood that one or more steps described herein can be performed in sequence or simultaneously.

For example, access to an external surface of the trachea and/or bronchus may be achieved through a surgical site at the anterior neck, or through a thoracotomy or thoracostomy site into the chest cavity. One or more steps can be performed with transcutaneous access, thoracoscopic access, and/or endoscopic access. One or more steps described herein can be performed with or without robotic assistance. For example, a method can be performed, at least in part, by a robotic device, with video-assisted thoracoscopic surgery (VATS) techniques, and/or with computer assistance.

A first longitudinal strip can be attached to a first region of tracheal and/or bronchial cartilage, and a second longitudinal strip can be attached to a second region of tracheal and/or bronchial cartilage (see FIG. 3). The first and second regions can be on opposite sides of a tracheal and/or bronchial wall. The attachment can be achieved with sutures. The sutures can be placed manually in an open surgical procedure, a minimally invasive surgical procedure, and/or endoscopically.

Excess portions of the longitudinal strips can be secured to the anatomy and/or removed from the body. For example, a given longitudinal strip may provide more length than is desired for a given patient or target anatomy. The excess length can be separated (e.g., cut) and removed from the body, so that only the portion secured to the patient remains. Additionally or alternatively, the excess length can be secured to another portion of the device and/or the anatomy (e.g., with one or more sutures). For example, a portion of a lateral strip can extend through an opening (e.g., extending through another lateral strip) and be folded back on itself. The lateral strip can be secured to itself in such a configuration, for example using one or more engagement elements described herein. Accordingly, the device can be customized to a particular patient's needs during a procedure.

Each of multiple first lateral strips extending from the first longitudinal strip can be attached to a corresponding one of multiple second lateral strips extending from the second longitudinal strip (see FIG. 4). Each pair of lateral strips can be attached to each other at one of a variety of configurations (e.g., tension settings). The configuration of any one pair of lateral strips can be the same or different than the configuration of any other pair of lateral strips. Accordingly, each pair of lateral strips can be attached, adjusted, and/or otherwise arranged independently of every other pair of lateral strips.

It will be understood that the attachment of lateral strips can be performed in any order, including incremental adjustments of any one pair of lateral strips. For example, a pair of lateral strips can be attached in a first (e.g., looser) configuration. Later, the same pair of lateral strips can be adjusted to a second (e.g., tighter) position, for example, after one or more other pairs of lateral strips have been attached and/or adjusted. Accordingly, the user can be provided with an ability to gradually make adjustments and confirm that a desired outcome is achieved.

Before, during, and/or after attachment to each other, the lateral strips can be attached to the tracheal and/or bronchial wall (see FIG. 5). The attachment can be achieved, for example, with sutures. The sutures can be placed manually in an open surgical procedure and/or endoscopically.

Excess portions of the lateral strips can be secured to the anatomy, secured to other portions of the devices, and/or removed from the body. For example, where the selected adjustment leaves a length of the lateral strip free (e.g., beyond the point of attachment), such a length can be secured to another portion of the device and/or the anatomy (e.g., with one or more sutures). Such a length can be secured at a nearby longitudinal strip to which it extends and/or folded back on itself and secured against the same or another lateral strip. Additionally or alternatively, where the selected adjustment leaves a length of the lateral strip free (e.g., beyond the point of attachment), such a length can be separated (e.g., cut) and removed from the body.

Where both a trachea and one or both bronchi are to be treated, the steps can be performed on a trachea and the one or both bronchi. For example, the above steps can be performed with respect to tracheal anatomy, and other steps can be performed with respect to bronchial anatomy, as described further herein.

It will be understood that the components of the device can be assembled at the target location (e.g., at the trachea and/or bronchus) or at least partially pre-assembled. For example, the sutures can be provided to the strips during surgery, the sutures can also be pre-threaded or otherwise coupled (e.g., adhered) onto the strips prior to delivery to a target location. In some examples, the sutures can be pre-coupled to the mesh of the strips, and the same sutures can be secured to the body anatomy upon or after delivery thereto.

By further example, while the lateral strips can be attached to each other at the target location, the lateral strips can alternatively be attached to each other prior to delivery to a target location. In some examples, the lateral strips can be pre-assembled, and the same lateral strips can be adjusted (e.g., tightened) upon delivery to a target location to provide the desired tension (e.g., after attachment of the longitudinal strips). As used herein, attachment of any two components to each other can include adjustment of the two components relative to each other and into a new configuration.

An airway support device can be used independently of another device. Alternatively, an airway support device can be implanted with another device. For example, an airway support device can be implanted with another device on an interior and/or exterior of the trachea and/or bronchus.

Various examples of aspects of the disclosure are described below as clauses for convenience. These are provided as examples, and do not limit the subject technology.

Clause A: an airway support device comprising: a first longitudinal strip for attachment to a first region of cartilage; a first lateral strip extending from the first longitudinal strip and having multiple first attachment members; a second longitudinal strip for attachment to a second region of cartilage; and a second lateral strip extending from the second longitudinal strip and having a second attachment member, wherein the second attachment member is configured to selectively engage one of the first attachment members to connect the first lateral strip to the second lateral strip in a corresponding one of multiple adjustable configurations.

Clause B: an airway support device comprising: a first longitudinal strip for attachment to a first region of cartilage; multiple first lateral strips, each of the first lateral strips extending from the first longitudinal strip and having a first attachment member; a second longitudinal strip for attachment to a second region of cartilage; and multiple second lateral strips, each of the second lateral strips extending from the second longitudinal strip and having a second attachment member; wherein each of the first attachment members is configured to engage a corresponding one of the second attachment members to hold the first longitudinal strip with respect to the second with tension across the first lateral strips and the second lateral strips.

Clause C: a method of implanting an airway support device, the method comprising: attaching a first longitudinal strip to a first cartilage region; attaching a second longitudinal strip to a second cartilage region; and connecting a first lateral strip extending from the first longitudinal strip to a second lateral strip extending from the second longitudinal strip, wherein tension across the first lateral strip and the second lateral strip holds the first cartilage region and the second cartilage region a distance away from each other.

One or more of the above clauses can include one or more of the features described below. It is noted that any of the following clauses may be combined in any combination with each other, and placed into a respective independent clause, e.g., clause A, B, or C.

Clause 1: the first longitudinal strip and the first lateral strip are formed from a first mesh; and the second longitudinal strip and the second lateral strip are formed from a second mesh.

Clause 2: the first attachment members comprise protrusions; and the second attachment member comprise an opening.

Clause 3: the first attachment members comprise openings; and the second attachment member comprises a protrusion.

Clause 4: the first lateral strip comprises a terminal end having a tapered shape.

Clause 5: the first lateral strip comprises a thread defining a terminal end of the first lateral strip opposite the first longitudinal strip.

Clause 6: suture markers along the first longitudinal strip and the second longitudinal strip, the suture markers indicating a target location for a suture.

Clause 7: reference markers evenly distributed along the first longitudinal strip, each of the reference markers being positioned a distance away from a corresponding one of the first lateral strips.

Clause 8: each of the first lateral strips is connectable to a corresponding one of the second lateral strips in a configuration that is independent of every other pair of first lateral strips and second lateral strips.

Clause 9: each of the first lateral strips is adjustably connectable to a corresponding one of the second lateral strips with a tension that is independent of a tension across every other pair of first lateral strips and second lateral strips.

Clause 10: the first longitudinal strip and the first lateral strip are formed from a first mesh; and the second longitudinal strip and the second lateral strip are formed from a second mesh.

Clause 11: the first region of cartilage is on a first side of a trachea; the second region of cartilage is on a second side of the trachea; the first lateral strips are first tracheal lateral strips; and the second lateral strips are second tracheal lateral strips; The airway support device of claim 9, further comprising: multiple first bronchial lateral strips, each of the first bronchial lateral strips extending from the first longitudinal strip and having a first bronchial attachment member; multiple second bronchial lateral strips, each of the second lateral strips extending from the second longitudinal strip and having a second bronchial attachment member; a third longitudinal strip for attachment to a first region of bronchial cartilage; multiple third bronchial lateral strips, each of the third lateral strips extending from the third longitudinal strip and having a third bronchial attachment member; a fourth longitudinal strip for attachment to a second region of bronchial cartilage; and multiple fourth lateral strips, each of the fourth lateral strips extending from the fourth longitudinal strip and having a fourth bronchial attachment member; wherein each of the first bronchial attachment members is configured to engage a corresponding one of the third bronchial attachment members; and wherein each of the second bronchial attachment members is configured to engage a corresponding one of the fourth bronchial attachment members.

Clause 12: the third longitudinal strip and the fourth longitudinal strip are connected to form a continuous strip.

Clause 13: attaching the first lateral strip or the second lateral strip to an airway wall connecting the first cartilage region and the second cartilage region together.

Clause 14: the distance is a first distance; and the method further comprises adjusting the tension across the first lateral strip and the second lateral strip to hold the first cartilage region and the second cartilage region a second distance away from each other, the second distance being different than the first distance.

Clause 15: the first cartilage region is a first tracheal cartilage region; the second cartilage region is a second tracheal cartilage region; the method further comprises: attaching the first longitudinal strip to a first region of bronchial cartilage extending from the first tracheal cartilage region; attaching the second longitudinal strip to a second region of bronchial cartilage extending from the second tracheal cartilage region; attaching a third longitudinal strip to a third region of bronchial cartilage; attaching a fourth longitudinal strip to a fourth region of bronchial cartilage, the third region of bronchial cartilage and the fourth region of bronchial cartilage being between the first region of bronchial cartilage and the second region of bronchial cartilage; connecting a third lateral strip extending from the first longitudinal strip to a fourth lateral strip extending from the third longitudinal strip; and connecting a fifth lateral strip extending from the second longitudinal strip to a sixth lateral strip extending from the fourth longitudinal strip.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. An airway support device comprising:
   a first longitudinal strip for attachment to a first region of cartilage;
   a first lateral strip extending from the first longitudinal strip and having multiple first attachment members;
   a second longitudinal strip for attachment to a second region of cartilage; and
   a second lateral strip extending from the second longitudinal strip and having a second attachment member, wherein the second attachment member is configured to selectively engage one of the first attachment members to connect the first lateral strip to the second lateral strip in a corresponding one of multiple adjustable configurations.

2. The airway support device of claim 1, wherein:
   the first longitudinal strip and the first lateral strip are formed from a first mesh; and
   the second longitudinal strip and the second lateral strip are formed from a second mesh.

3. The airway support device of claim 1, wherein:
   the first attachment members comprise protrusions; and
   the second attachment member comprise an opening.

4. The airway support device of claim 1, wherein:
   the first attachment members comprise openings; and
   the second attachment member comprises a protrusion.

5. The airway support device of claim 1, wherein the first lateral strip comprises a terminal end having a tapered shape.

6. The airway support device of claim 1, wherein the first lateral strip comprises a thread defining a terminal end of the first lateral strip opposite the first longitudinal strip.

7. The airway support device of claim 1, further comprising suture markers along the first longitudinal strip and the second longitudinal strip, the suture markers indicating a target location for a suture.

8. The airway support device of claim 1, wherein the airway support device comprises fabrics forming a mesh, the fabrics being fluorescent.

9. An airway support device comprising:
a first longitudinal strip for attachment to a first region of cartilage;
multiple first lateral strips, each of the first lateral strips extending from the first longitudinal strip and having a first attachment member;
a second longitudinal strip for attachment to a second region of cartilage; and
multiple second lateral strips, each of the second lateral strips extending from the second longitudinal strip and having a second attachment member;
wherein each of the first attachment members is configured to engage a corresponding one of the second attachment members to hold the first longitudinal strip with respect to the second longitudinal strip with tension across the first lateral strips and the second lateral strips.

10. The airway support device of claim 9, wherein each of the first lateral strips is connectable to a corresponding one of the second lateral strips in a configuration that is independent of every other pair of first lateral strips and second lateral strips.

11. The airway support device of claim 9, wherein each of the first lateral strips is adjustably connectable to a corresponding one of the second lateral strips with a tension that is independent of a tension across every other pair of first lateral strips and second lateral strips.

12. The airway support device of claim 9, wherein:
the first longitudinal strip and the first lateral strip are formed from a first mesh; and
the second longitudinal strip and the second lateral strip are formed from a second mesh.

13. The airway support device of claim 9, wherein:
the first region of cartilage is on a first side of a trachea;
the second region of cartilage is on a second side of the trachea;
the first lateral strips are first tracheal lateral strips; and
the second lateral strips are second tracheal lateral strips.

14. The airway support device of claim 9, further comprising:
multiple first bronchial lateral strips, each of the first bronchial lateral strips extending from the first longitudinal strip and having a first bronchial attachment member;
multiple second bronchial lateral strips, each of the second lateral strips extending from the second longitudinal strip and having a second bronchial attachment member;
a third longitudinal strip for attachment to a first region of bronchial cartilage;
multiple third bronchial lateral strips, each of the third lateral strips extending from the third longitudinal strip and having a third bronchial attachment member;
a fourth longitudinal strip for attachment to a second region of bronchial cartilage; and
multiple fourth lateral strips, each of the fourth lateral strips extending from the fourth longitudinal strip and having a fourth bronchial attachment member;
wherein each of the first bronchial attachment members is configured to engage a corresponding one of the third bronchial attachment members; and
wherein each of the second bronchial attachment members is configured to engage a corresponding one of the fourth bronchial attachment members.

15. The airway support device of claim 14, wherein the third longitudinal strip and the fourth longitudinal strip are connected to form a continuous strip.

16. A method of implanting an airway support device, the method comprising:
attaching a first longitudinal strip to a first cartilage region;
attaching a second longitudinal strip to a second cartilage region; and
connecting a first lateral strip extending from the first longitudinal strip to a second lateral strip extending from the second longitudinal strip, wherein tension across the first lateral strip and the second lateral strip holds the first cartilage region and the second cartilage region a distance away from each other.

17. The method of claim 16, further comprising attaching the first lateral strip or the second lateral strip to an airway wall connecting the first cartilage region and the second cartilage region together.

18. The method of claim 16, wherein:
the distance is a first distance; and
the method further comprises adjusting the tension across the first lateral strip and the second lateral strip to hold the first cartilage region and the second cartilage region a second distance away from each other, the second distance being different than the first distance.

19. The method of claim 16, wherein:
the first cartilage region is a first tracheal cartilage region;
the second cartilage region is a second tracheal cartilage region;
the method further comprises:
attaching the first longitudinal strip to a first region of bronchial cartilage extending from the first tracheal cartilage region;
attaching the second longitudinal strip to a second region of bronchial cartilage extending from the second tracheal cartilage region;
attaching a third longitudinal strip to a third region of bronchial cartilage;
attaching a fourth longitudinal strip to a fourth region of bronchial cartilage, the third region of bronchial cartilage and the fourth region of bronchial cartilage being between the first region of bronchial cartilage and the second region of bronchial cartilage;
connecting a third lateral strip extending from the first longitudinal strip to a fourth lateral strip extending from the third longitudinal strip; and
connecting a fifth lateral strip extending from the second longitudinal strip to a sixth lateral strip extending from the fourth longitudinal strip.

20. The method of claim 19, wherein the third longitudinal strip and the fourth longitudinal strip are connected to form a continuous strip.

* * * * *